United States Patent [19]
Marquis et al.

[11] Patent Number: 5,216,182
[45] Date of Patent: Jun. 1, 1993

[54] PREPARATION OF MONO EPOXIDES AND TERTIARY BUTYL ALCOHOL USING REGENERATED CATALYST

[75] Inventors: Edward T. Marquis, Austin, Tex.; Robert A. Meyer, Ballwin, Mo.

[73] Assignee: Texaco Chemical Company, White Plains, N.Y.

[21] Appl. No.: 933,936

[22] Filed: Aug. 24, 1992

[51] Int. Cl.$^5$ .................. C07D 301/14; C07D 303/04
[52] U.S. Cl. ..................... 547/529; 502/24; 502/33; 508/909.8
[58] Field of Search ........................... 549/529

[56] References Cited

U.S. PATENT DOCUMENTS

| | | | |
|---|---|---|---|
| 3,931,044 | 1/1976 | Maurin | 549/529 |
| 4,598,057 | 7/1986 | Isaacs | 549/529 |
| 4,626,596 | 12/1986 | Marquis et al. | 549/529 |
| 5,101,052 | 3/1992 | Meyer et al. | 549/529 |
| 5,107,067 | 4/1992 | Marquis et al. | 549/529 |

Primary Examiner—Joseph E. Evans
Attorney, Agent, or Firm—James L. Bailey; Kenneth R. Priem; Carl G. Ries

[57] ABSTRACT

In the preparation of tertiary butyl alcohol and a linear $C_3$–$C_{12}$ mono epoxide by the epoxidation reaction of a linear $C_3$–$C_{12}$ alpha mono olefin with tertiary butyl hydroperoxide in solution in tertiary butyl alcohol in the presence of a catalytic amount of a soluble complex of molybdenum with ethylene glycol, a portion of the catalyst that is used is a recycle (final) ethylene glycol solution of a complex of ethylene glycol with ammonium-containing molybdenum compounds prepared from ethylene glycol and a precipitate of solid ammonium-containing molybdenum compounds formed by saturating a heavy distillation fraction with ammonia to thereby form a liquid amination product containing a precipitate of solid ammonium-containing molybdenum compounds; the heavy distillation fraction being obtained by distillation of the epoxidation reaction product.

9 Claims, 1 Drawing Sheet

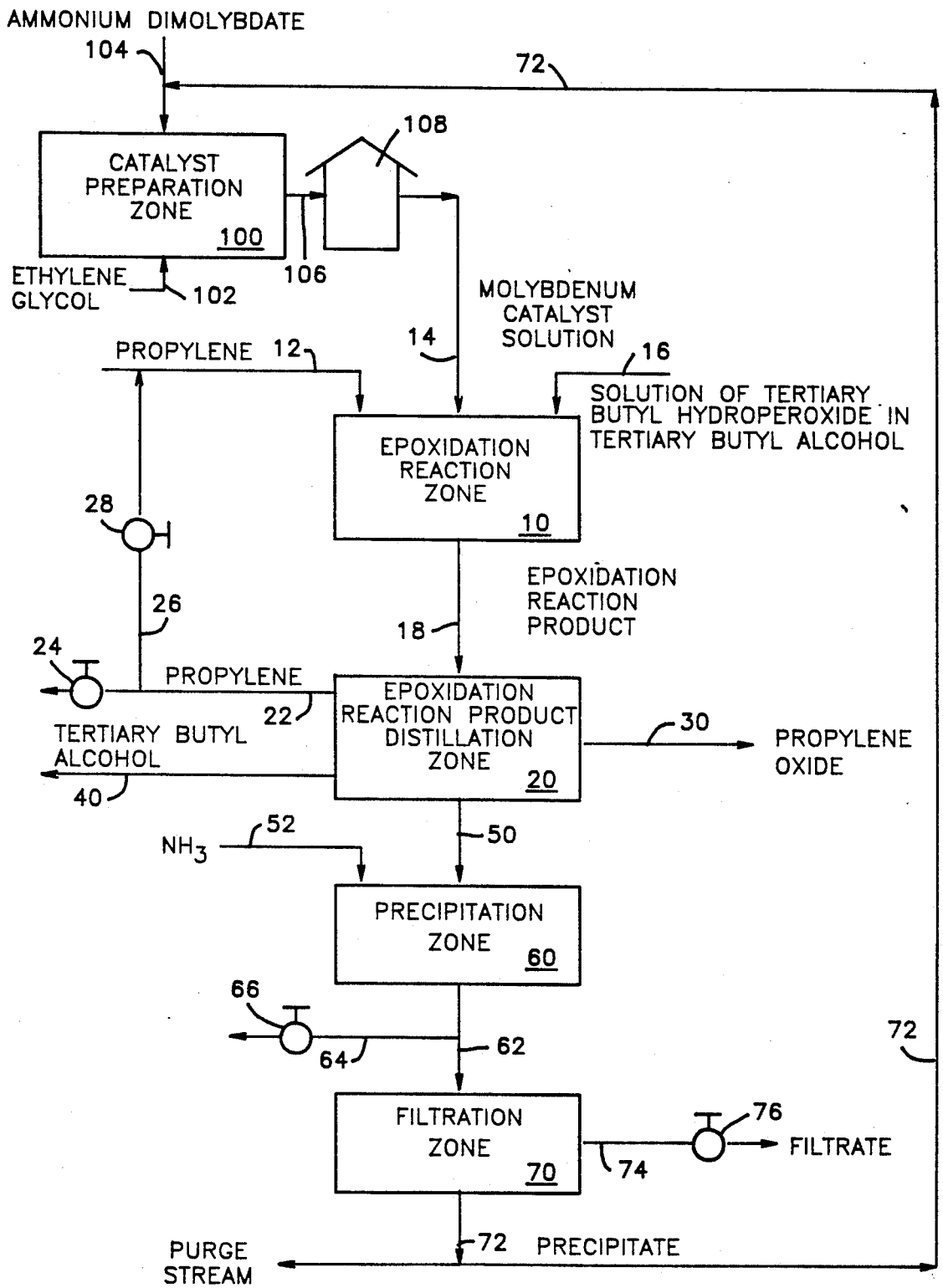

PREPARATION OF MONO EPOXIDES AND TERTIARY BUTYL ALCOHOL USING REGENERATED CATALYST

BACKGROUND OF THE INVENTION

Technical Field of the Invention

This invention relates to an improvement in the method for preparing an epoxide of an alpha olefin such as propylene oxide and tertiary butyl alcohol from a $C_3$ to $C_{12}$ alpha olefin such as propylene and tertiary butyl hydroperoxide. More particularly, this invention relates to a method for the preparation of propylene oxide and tertiary butyl alcohol from propylene and tertiary butyl hydroperoxide using a regenerated catalyst. Also, this invention relates to a process for preparing an epoxide of an alpha olefin such as propylene oxide and tertiary butyl alcohol by the molybdenum catalyzed reaction of a $C_3$ to $C_{12}$ linear alpha olefin such as octene-1 or propylene With tertiary butyl hydroperoxide wherein a distillation fraction obtained from the epoxidation reaction mixture which contains residual molybdenum catalyst is reacted with ammonia in liquid phase to provide a precipitate which is then reacted with ethylene glycol to provide a regenerated molybdenum catalyst which is used as a portion of the catalyst requirement to catalyze the reaction of the linear alpha olefin with tertiary butyl hydroperoxide.

PRIOR ART

Kollar U.S. Pat. Nos. 3,350,422 and 3,351,635 disclose and describe a method for the preparation of olefin epoxides and alcohols by the molybdenum catalyzed reaction of an olefin with a tertiary alkyl peroxide. It was recognized early on, as exemplified by Kollar U.S. Pat. Nos. 3,860,882, 3,947,500 and 3,947,501 that side reactions occur during the epoxidation of an olefin with a hydroperoxide in the presence of a soluble molybdenum catalyst that give rise to oxygen-containing by-products including acids, esters and ketones. In Kollar U.S. Pat. Nos. 3,860,662, 3,947,500 and 3,947,501, Kollar sought to improve the efficiency of the epoxidation reaction by reducing the acidic characteristics of the epoxidation reaction product by adding a basic material to the reaction mixture, by adding a chemical reducing agent to the reaction mixture or by hydrogenating the reaction mixture in the presence of a hydrogenation catalyst.

In British Pat. No. 1,298,253, it was proposed to conduct the reaction on a continuous basis using an excess of tertiary butyl hydroperoxide in a first reaction zone and added propylene in a second reaction zone.

More recently, Marquis et al. in U.S. Pat. No. 4,891,437 have proposed to improve the efficiency of the process and to reduce by-product formation by the molybdenum catalyst catalyzed reaction of an olefin with tertiary hydroperoxide or tertiary butyl hydroperoxide in a reaction medium containing more than about 60 wt. % of polar components. Marquis et al. in U.S. Pat. No. 4,626,596 have also proposed the use of a molybdenum/alkylene glycol complex prepared in a described manner in the preparation of propylene oxide and tertiary butyl alcohol from propylene and tertiary butyl hydroperoxide. Marquis et al. have also proposed the use of a molybdenum/sodium/ethylene glycol catalyst for the reaction in U.S. Pat. No. 4,845,251.

Catalyst Preparation

It was also recognized early on that the manner in which the molybdenum catalyst was prepared would have an important bearing on the efficiency of the reaction. Thus, in Kollar U.S. Pat. No. 3,362,972, proposed the preparation of molybdenum catalysts by the reaction of a molybdenum salt with a carboxylic acid.

Mattucci et al. in U.S. Pat. No. 3,668,227 disclose the preparation of soluble molybdenum compounds by reacting an organic molybdenum oxide with a compound having vicinal hydroxyl groups (e.g., by the reaction of molybdenum acetyl acetonate with isobutylene glycol). The patentees stated that in formation, or in use, the molybdenum compounds undergo prototrophic rearrangement to form molybdenum diol complexes having the formula given in the patent.

Bonetti in U.S. Pat. No. 3,480,563 propose the preparation of organic soluble molybdenum catalysts by the reaction of molybdenum trioxide with an acyclic alcohol or a polyalkylene glycol monoether.

Molybdenum salt catalysts were prepared by Lines et al. in U.S. Pat. No. 3,953,362 by the reaction of a molybdenum oxide with hydrogen peroxide and an amine in the optional presence of water or an alkylene glycol.

In Hagstrom et al. U.S. Pat. No. 3,991,090, propose the preparation of molybdenum derived compounds by the reaction of a molybdenum oxide with an organic compound containing vicinal hydroxyl groups in the presence of a hydrohalide acid. Again, the preparation of molybdenum-alkylene glycol complexes having the formula of the type disclosed by Mattucci et al. in U.S. Pat. No. 3,668,227 is stated to occur.

Subsequently, Marquis et al. sought to provide improved molybdenum catalysts such as catalysts prepared in accordance with U.S. Pat. No. 4,626,596 by the reaction of an ammonium-containing molybdenum compound with an alkylene glycol in the presence of a controlled amount of water under recited reaction conditions. Marquis et al. also disclose the preparation of storage stable molybdenum/alkanol complexes by reacting an ammonium molybdate with an alkanol in the presence of controlled amounts of water under recited reaction conditions in U.S. Pat. No. 4,650,886. Marquis et al. in U.S. Pat. No. 4,654,427 further describe the preparation of storage stable solutions of molybdenum/alkanol complexes by reacting a molybdenum oxide, ammonium hydroxide, and a straight chain or branched chain $C_6$–$C_{13}$ alkanol. In Marquis et al. U.S. Pat. No. 4,703,027, disclose complexes prepared by reacting a solid ammonium molybdate and a solid alkali metal molybdate with ethylene glycol under controlled reaction conditions. Also, in Marquis et al. U.S. Pat. No. 4,758,681, a method of preparing a molybdenum catalyst is disclosed wherein ethylene glycol is reacted with an ammonium dimolybdate under recited reaction conditions. Also, in Marquis et al. U.S. Pat. No. 5,107,067, propose the preparation of a catalyst by the reaction of an ammonium-containing molybdenum compound with an alkylene glycol in the presence of water followed by mild stripping of water subsequent to the formation of the molybdenum/alkylene glycol complex.

Molybdenum Recovery

It is conventional practice to charge the epoxidation reaction mixture to a distillation zone and there separate it into desired distillation fractions such as a recycle propylene fraction, a product propylene oxide fraction, a tertiary butyl alcohol fraction and a heavy distillation fraction containing oxygenated by-products such as acids, esters and ketones and catalyst residue. The presence of the molybdenum compounds in this heavy distillation fraction represents a problem insofar as further workup or disposal of the fraction is concerned.

It was known from the workup of molybdenum-catalyzed coal liquefaction reaction products that molybdenum could be recovered by treating the process residue with an alkali to form water soluble molybdates which could then be roasted and leached to form a product which could thereafter be extracted with water, acidified and ammoniated to form a molybdenum-bearing precipitate which could be dissolved in ammonium hydroxide to form a solution to be used to catalyze coal liquefaction. See, for example, Sebenik et al. U.S. Pat. No. 4,374,100.

Insofar as the epoxidation of olefins is concerned, Khuri et al in U.S. Pat. No. 3,763,303 propose the process for the recovery of molybdenum from the epoxidation reaction product residue involving the steps of water extraction to obtain soluble molybdenum compounds, evaporation of the water to form a molybdenum-containing residue and calcination of the molybdenum-containing residue.

Lamke U.S. Pat. No. 3,887,361 propose to recover molybdenum by heating the reaction residue effluent at an elevated temperature in a closed reaction vessel in order to precipitate the molybdenum compounds. Poenisch in U.S. Pat. No. 4,485,074 propose to first add water to the organic molybdenum-containing solution and to then heat the resultant aqueous mixture under pressure in order to precipitate the molybdenum compounds.

Meyer et al. in U.S. Pat. No. 5,093,509 propose to recover molybdenum by a process that uses a synthetic high surface area amorphous magnesium silicate as a solid adsorbent. In Meyer et al. U.S. Pat. No. 5,101,052, propose to recover molybdenum by precipitating molybdenum from a residual heavy distillation fraction with ammonia. Smith et al. in U.S. Pat. No. 5,128,492 describe molybdenum recovery by hydrogenation. British Pat. No. 1,317,480 also proposes to recover molybdenum compounds by a process involving the use of water or aqueous ammonia to treat the heavy distillation fraction in order to form an aqueous phase containing molybdenum from which the molybdenum can subsequently be recovered as molybdenum trioxide.

Catalyst Regeneration

It has also been recognized that, where feasible, it would be desirable to regenerate at least a portion of the molybdenum contained in the epoxidation reaction product for reuse as catalyst for epoxidizing the reaction of an olefin with a hydroperoxide.

Thus, Sorgenti in U.S. Pat. No. 3,573,226 proposed a method for regenerating molybdenum contained in the heavy distillation fraction obtained by distillation of the epoxidation reaction product. Sorgenti proposes to utilize a bottoms fraction resulting from the distillation of the epoxidation reaction product which contains small amounts of tertiary butyl alcohol, unreacted tertiary butyl hydroperoxide, acidic compounds, polyhydric compounds and used catalysts by adding metallic finely divided molybdenum powder to the bottoms fraction followed by heating of the resultant mixture in order to solubilize the molybdenum and provide a fraction which could be recycled to the reactor to provide for the conversion of propylene and tertiary butyl hydroperoxide to propylene oxide and tertiary butyl alcohol with a conversion of about 81 mol % of the hydroperoxide and a selectivity of 75% to propylene oxide, based on the hydroperoxide charged.

Levine et al. in U.S. Pat. No. 3,819,663 propose to take the heavy distillation fraction recovered from by distillation from the epoxidation reaction and subject it to further fractionation in a wiped film evaporator to obtain either a liquid molybdenum concentrate that can be mixed with tertiary butanol to provide a regenerated catalyst or a molybdenum powder that can be mixed with tertiary butyl alcohol, tertiary butyl hydroperoxide and monopropylene glycol to provide a regenerated catalyst. Three techniques for regenerating catalyst are disclosed in Maurin U.S. Pat. No. 3,931,044. In accordance with one embodiment, the residue fraction resulting from distillation of the epoxidation reaction mixture is calcined to form molybdenum trioxide which is then dissolved in aqueous ammonia to provide ammonia molybdate which can then be treated with a polyalcohol such as methyl-2,3-butane diol to provide a soluble molybdenum compound. In accordance with the second embodiment, the spent molybdenum-containing fraction is treated with an aqueous solution of ammonia without calcination to form an ammonium molybdate which is then treated with a polyalcohol such as methyl-2,3-butane diol to form a soluble molybdenum compound. In accordance with a third embodiment, the heavy distillation fraction is directly treated with gaseous ammonia to form a precipitate of ammonium molybdate which is dissolved in a solvent such as acetone and then treated with a polyalcohol such as methyl-2,3-butane diol. A regeneration process wherein the molybdenum is thermally precipitated from the heavy distillation fraction and then reacted with an alcohol and an organic dicarboxylic acid is disclosed in Isaacs U.S. Pat. No. 4,598,057.

Marquis et al. in U.S. Pat. No. 5,093,506 disclose a process wherein a distillation fraction containing tertiary butyl hydroperoxide, tertiary butyl alcohol, and carboxylic acid contaminants is partially neutralized with calcium oxide or calcium hydroxide to form a precipitate which is removed and the resultant supernatant liquid is then recycled to the epoxidation reactor for use as an oxidant/solvent without causing precipitation of molybdenum in the reaction zone.

SUMMARY OF THE INVENTION

The present invention is directed to a method for the preparation of tertiary butyl alcohol and propylene oxide by the reaction of an epoxide of a $C_3$–$C_{12}$ linear alpha mono olefin such as a $C_3$–$C_{12}$ linear alpha mono olefin such as octene-1 or propylene with tertiary butyl hydroperoxide in an epoxidation reaction zone in solution in tertiary butyl alcohol in the presence of a soluble complex of molybdenum with ethylene glycol to provide an epoxidation reaction product which is fractionated to provide a distillate olefin fraction, a distillate epoxide fraction, a distillate tertiary butyl alcohol fraction and a heavy liquid distillation fraction composed primarily of tertiary butyl hydroperoxide, tertiary butyl alcohol, oxygen-containing impurities and dissolved molybdenum-ethylene glycol catalyst complex wherein the heavy distillation fraction is saturated with ammonia in a precipitation zone to provide a solid ammonium-containing molybdenum precipitate which is recovered and reacted in a catalyst regeneration zone with substantially anhydrous ethylene glycol to form an ethylene glycol solution of a complex of ethylene glycol with ammonium-containing compounds present in the precipitate and this solution, after removal of volatile by-products is recycled for use as a catalyst for the conversion of additional mono olefin and additional tertiary butyl hydroperoxide to tertiary butyl alcohol and mono olefin epoxide.

More particularly, the process of the present invention is a process wherein:

a. anhydrous ethylene glycol and anhydrous ammonium dimolybdate are charged to a catalyst preparation reactor in an amount sufficient to provide about 7 to about 20 moles of ethylene glycol per gram atom of molybdenum contained in the ammonium dimolybdate;

b. the resultant mixture is heated at a pressure of about 0 to about 3,000 psig in a reaction temperature of about 70° to about 250° C. for about 1 to 2 hours in order to form a solids-free solution of a complex of ethylene glycol with ammonium dimolybdate;

c. the solids-free solution of the complex of ethylene glycol with the ammonium dimolybdate is held at a temperature of about 90° to about 110° C. for a time within the range of 0.5 to 5 hours sufficient to permit vaporization and removal of volatile by-products, including water, by an amount sufficient to provide an initial ethylene glycol solution containing about 16 to about 52 wt. % of said complex of ethylene glycol with said ammonium dimolybdate and having a molybdenum content of about 6 to about 20 wt. % and a water concentration of about 0.5 to 6 wt. %;

d. a tertiary butyl alcohol solution of tertiary butyl hydroperoxide and propylene charged to an epoxidation reaction zone together with a catalytic amount of a catalyst mixture composed of said initial ethylene glycol solution of said complex with ethylene glycol with said ammonium dimolybdate and a final ethylene glycol solution of a complex of ethylene glycol with ammonium-containing molybdenum compounds derived from a precipitate of solid ammonium containing molybdenum compounds, the initial molar ratio of propylene to tertiary butyl alcohol solution of active tertiary butyl hydroperoxide being about 1.05:1 to about 2:1 and containing about 100 to about 600 ppm of catalyst mixture;

e. establishing epoxidation reaction conditions in the epoxidation reaction zone including a temperature of about 50° to about 180° C., and a residence time of about 1 to about 5 hours to thereby react the propylene with the tertiary butyl hydroperoxide to provide an epoxidation reaction product comprising unreacted propylene, unreacted tertiary butyl hydroperoxide, propylene oxide, tertiary butyl alcohol, dissolved molybdenum ethylene glycol catalyst complex and oxygen-containing impurities;

f. resolving the epoxidation reaction products in a distillation zone into distillation fractions including a distillate propylene fraction, a distillate propylene oxide fraction, a distillate tertiary butyl alcohol fraction and a heavy liquid distillation fraction composed primarily of tertiary butyl hydroperoxide, tertiary butyl alcohol, oxygen-containing impurities and dissolved molybdenum-ethylene glycol catalyst complex;

g. charging the heavy distillation fraction to a precipitation zone and saturating it therein with ammonia to form a liquid amination product containing a precipitate of solid ammonium-containing molybdenum compounds;

h. charging the amination product to a separation zone and therein separating the solid ammonium-containing molybdenum precipitate from the liquid medium;

i. recovering the solid ammonium-containing molybdenum precipitate;

j. charging the recovered solid ammonium-containing molybdenum precipitate to a catalyst regeneration zone and mixing it therein with an amount of substantially anhydrous ethylene glycol sufficient to provide about 7 to about 20 moles of ethylene glycol per gram atom of molybdenum contained in the solid ammonium-containing molybdenum precipitate to form an ethylene glycol feed mixture;

k. heating the ethylene glycol feed mixture in a catalyst regeneration zone at a pressure of about 0 to about 3,000 psig and a reaction temperature of about 70° to about 250° C. for a time within the range of about 1 to 2 hours sufficient to form a substantially solids-free ethylene glycol solution of a complex of ethylene glycol with ammonium-containing compounds in said solid ammonium-containing molybdenum precipitate;

l. holding said solids-free solution of said complex of ethylene glycol with said ammonium-containing compounds in said catalyst regeneration zone at a temperature of about 90° to about 110° C. for a time, within the range of about 0.5 to about 5 hours, sufficient to permit vaporization and removal of volatile by-products, including water, by an amount sufficient to provide a final ethylene glycol solution containing about 17 to about 52 wt. % of said complex of ethylene glycol with said ammonium-containing molybdenum compounds and having a molybdenum content of about 6 to about 20 wt. % and a water concentration of about 0.5 to about 6%; and m. charging said thus-prepared final ethylene glycol solution to said epoxidation reaction zone as said final ethylene glycol solution of a complex of ethylene glycol with ammonium-containing molybdenum compounds derived from a precipitate of solid ammonium-containing molybdenum compounds.

Still more preferably, the process of the present invention is conducted in the above described manner on a continuous basis.

DETAILED DESCRIPTION OF THE PREFERRED EMBODIMENT

Starting Materials

The starting materials for the present invention are a $C_3$-$C_{12}$ linear alpha mono olefin, tertiary butyl hydroperoxide, ethylene glycol, an initial ethylene glycol solution of a complex of ethylene glycol with ammonium dimolybdate and a final ethylene glycol solution of a complex of ethylene glycol with ammonium-containing molybdenum compounds derived from a precipitate of solid ammonium-containing molybdenum compounds.

The linear alpha olefins to be used as feedstocks in accordance with the present invention are unbranched linear mono olefins containing from 3 to 12 carbon atoms in the molecule including compounds such as propylene, butene-1, pentene-1, hexene-1, octene-1, dodecene-1, etc. A preferred mono olefin is propylene.

The tertiary butyl hydroperoxide that is used may be a standard industrial grade of tertiary butyl hydroperoxide prepared, for example, by the oxidation of isobutane with oxygen to provide as a reaction product, a solution of tertiary butyl hydroperoxide and tertiary butyl alcohol.

The ethylene glycol is preferably an industrial grade of ethylene glycol that is substantially anhydrous. An industrial grade of ammonium dimolybdate may also be used.

Preparation of the Initial Ethylene Glycol Solution

The starting materials for the preparation of the initial ethylene glycol solution are ethylene glycol and ammonium dimolybdate. The substantially anhydrous ethylene glycol and ammonium dimolybdate are charged to a catalyst preparation zone in amounts sufficient to provide a molar ratio of about 7 to about 20 moles of ethylene glycol per gram atom of molybdenum contained in the ammonium dimolybdate. The resultant feed mixture is heated at a temperature of about 80° to about 130° C. and more preferably at a temperature of about 90° to about 100° C. at a pressure of about 0 to about 3,000 psig, and preferably about 0 psig to thereby form a solution of a complex of ethylene glycol with the ammonium dimolybdate in ethylene glycol. The resultant solution is held at a temperature of about 90° to about 120° C. for about 0.5 to about 5 hours sufficient to permit volatilization of volatile reaction components including water and ammonia so as to provide an initial ethylene glycol solution containing about 16 to about 52 wt. % of the complex of ethylene glycol with the ammonium dimolybdate and having a molybdenum content of about 6 to about 20 wt. % and a water concentrate of about 0.5 to about 6 wt. %.

Preparation of the Final Ethylene Glycol Complex

The final ethylene glycol complex is also prepared in the manner described above for the preparation of the initial ethylene glycol solution. However, the source of the molybdenum is not the ammonium dimolybdate specified above but, instead, is a precipitate of a solid ammonium-containing molybdenum compound prepared and obtained in a manner to be described.

Epoxidation

In general, the alpha olefin is reacted with tertiary butyl hydroperoxide in solution in tertiary butyl alcohol in the presence of a catalyst mixture composed of the initial ethylene glycol solution and the final ethylene glycol solution by a process of the type disclosed in Kollar U.S. Pat. No. 3,351,635, such as a process of the type disclosed in Marquis et al. U.S. Pat. Nos. 4,845,251, 4,891,437 or 5,107,067.

In particular, the alpha olefin will be used in the form of an anhydrous olefin and the tertiary butyl hydroperoxide will be charged in the form of a solution of about 40 to about 75 wt. % of tertiary butyl hydroperoxide in tertiary butyl alcohol. The reactants will be charged in amounts such that the reaction mixture contains from about 200 to about 600 ppm of the solubilized molybdenum catalyst and such that the molar ratio of alpha olefin to tertiary butyl hydroperoxide is within the range of about 1.05:1 to about 2:1 and, more preferably, within the range of from about 1.05:1 to about 1.8:1, and still more preferably in the range of from about 1.05:1 to about 1.35:1. When the feed materials to the epoxidation reaction zone are charged in the described fashion, the resultant reaction mixture will initially contain more than about 60 wt. % of polar components (tertiary butyl alcohol and tertiary butyl hydroperoxide). The olefin epoxide that is formed during the epoxidation reaction is also a polar material.

The epoxidation reaction may suitably be conducted at a temperature within the range of about 50° to about 180° C., preferably within the range of about 90° to about 140° C., and more preferably within the range from about 100° to about 120° C.

The reaction is suitably conducted at a pressure sufficient to maintain the reactants in liquid phase. Thus, for the higher alpha olefins such as octene-1, the reaction can be conducted at atmospheric pressure However, a superatmospheric pressure is required for the more volatile lower alpha olefins, such as propylene and butene-1. In this situation, the lower pressure is suitably about 500 psig.

Higher pressures such as pressures within the range of about 500 to about 3,000 psig. may be used if desired. Reaction time may suitably vary from about 0.5 to about 5 hours, and more preferably from about 1.5 to about 2 hours. The reaction may be conducted in a single reaction zone or in a plurality of reaction zones as described, for example, in Marquis et al. U.S. Pat. No. 4,891,437.

Molybdenum Recovery

In accordance with the present invention, the epoxidation reaction product formed in the above described fashion, is charged to a distillation zone and resolved therein into a plurality of fractions including a distillate olefin fraction, a distillate olefin epoxide fraction, a distillate tertiary butyl alcohol fraction, a heavy liquid distillation fraction containing tertiary butyl alcohol, oxygen-containing impurities and dissolved molybdenum-ethylene glycol catalyst complex.

The heavy distillation fraction may then be treated, as for example, in the manner disclosed in Meyer et al. U.S. Pat. No. 5,101,052.

In accordance with the present invention, a heavy distillation fraction comprising tertiary butyl hydroperoxide, tertiary butyl alcohol and impurities including about 0.4 to about 0.8 wt. % of dissolved molybdenum catalyst and lower aliphatic carboxylic acids resulting from the removal of olefin, olefin epoxide and tertiary butyl alcohol from an epoxidation reaction product is charged to a precipitation zone which may suitably comprise a reactor, such as an autoclave, provided with suitable agitating means (e.g., an impeller), temperature control means such as a jacket or coils through which a liquid heat exchange medium can be circulated, charge lines for the heavy distillation fraction and for the ammonia and a discharge line for withdrawal of the treated product. Within the precipitation zone the ammonia will react with the molybdenum compounds present in the heavy distillation fraction to form a reaction product comprising a molybdenum-containing precipitate that can be withdrawn from the precipitation zone. The precipitate can be removed in any desired manner in a precipitate removal zone (e.g., by filtration, centrifugation, etc.).

It has been discovered in accordance with the present invention that when the heavy distillation fraction contains only about 0.8 wt. % or less of molybdenum (e.g., 0.4 to 0.8 wt. %), the precipitation of the molybdenum compounds will be essentially complete in that that precipitate will contain substantially all of the molybdenum charged to the precipitation zone. It has been discovered that when heavy distillation fractions containing larger amounts of molybdenum are used, an undesirable higher percentage of the molybdenum will remain dissolved in the treated heavy fraction.

The heavy distillation fraction will normally contain less than about 1 wt. % of water and, therefore, ammonia should be used, as such, rather than in the form of an aqueous ammoniacal solution. The ammonia should preferably be used in an amount which is equivalent to the amount of molybdenum in the heavy distillation fraction and, preferably, an excess of ammonia will be used, such as about 1 to about 200 moles of ammonia per gram atom of molybdenum present in the heavy distillation fraction. Preferably, the heavy distillation fraction is saturated with ammonia.

The precipitation reaction can be conducted under ambient conditions of temperature and pressure, although somewhat higher temperatures and pressures may be used, if desired, such as temperatures within the range of about 20° to 250° C. and pressures within the range of about 0 to 3,000 psig. The contact time should be sufficient to insure that the precipitation reaction goes to completion (e.g., 0.2 to 2 hours).

After the precipitation reaction is completed, the mixture of precipitate and treated heavy distillation fraction is withdrawn from the precipitation zone for removal of the precipitate. The precipitate can be removed in any desired manner, e.g., filtration, centrifugation, evaporation, etc. Since the precipitate constitutes only a minor amount of the mixture of precipitate and treated heavy distillation fraction, filtration is preferred.

The filtrate obtained by the practice of the present invention will contain only a residual amount of molybdenum (e.g., from 10 to 100 ppm). For example, it can be charged to a boiler as a fuel, or further treated (e.g., by vacuum distillation for the recovery of at least a portion of the tertiary butyl alcohol and/or tertiary butyl hydroperoxide contained therein.

The precipitate will normally contain about 40 to about 58 wt. % of molybdenum.

Catalyst Regeneration

In accordance with the present invention, the solid ammonium-containing molybdenum precipitate is charged to a catalyst regeneration zone where it is mixed with substantially anhydrous ethylene glycol in an amount sufficient to provide about 7 to about 20 moles of ethylene glycol per gram atom of molybdenum contained in the solid ammonium-containing molybdenum precipitate to thereby form an ethylene glycol feed mixture. A preferred ratio of ethylene glycol to gram atoms of molybdenum is within the range of about 8:1 to about 16:1. The water content of the ethylene glycol feed mixture should preferably be within the range of about 0.1 to about 2 wt. %. The resultant mixture of ethylene glycol with precipitate is heated in the catalyst regeneration zone at a temperature within the range of about 50° to about 150° C., and more preferably within the range of about 90° to about 120° C. and a pressure of about 0 to about 3,000 psig., and preferably about 0 psig., for a period of time within the range of about 0.2 to 2 hours, and preferably 0.5 to 1.5 hours.

In a preferred embodiment, the reactants are heated to about 90° to about 120° C. for about 1 hour at ambient pressure, cooled and then subjected to a vacuum of 10 to 100 mm Hg for 30 to 60 minutes to remove water, ammonia and excess ethylene glycol. Sufficient volatile materials should be removed overhead so as to provide a liquid product containing from about 80 to about 95 wt. % of the initial charge and should have a water content of about 0.1 to about 2 wt. % and contain from about 6 wt. % to about 20 wt. % of molybdenum.

The resultant thus formed final ethylene glycol solution of a complex of ethylene glycol with ammonium-containing molybdenum compounds can then be recycled to the epoxidation reaction zone as the final ethylene glycol solution of a complex of ethylene glycol with ammonium-containing molybdenum compounds derived from a precipitate of solid ammonium-containing molybdenum compounds. Preferably, the catalyst mixture will contain from about 40 to about 60 wt. % of the initial ethylene glycol solution and, correspondingly, from about 60 to about 40 wt. % of the final ethylene glycol solution.

BRIEF DESCRIPTION OF THE DRAWING

In the drawing, the Figure is a schematic drawing of a preferred reaction and purification sequence that may be used in the practice of the present invention.

DESCRIPTION OF THE PREFERRED EMBODIMENT

Turning now to the drawing, there is shown a schematic flow sheet illustrating the preferred method of practicing the process of the present invention.

In accordance with the present invention, a catalyst preparation zone 100 is provided to which substantially anhydrous ethylene glycol is charged by a line 102 and to which ammonium dimolybdate is charged by way of a line 104. The ethylene glycol and ammonium dimolybdate are charged in a manner such that the resultant mixture of ethylene glycol with ammonium dimolybdate will contain from about 7 to about 20 moles of ethylene glycol per gram atom of molybdenum in the ammonium dimolybdate and, more preferably, from about 8 to about 16 moles of ethylene glycol per gram atom of molybdenum contained in the ammonium dimolybdate.

The resultant mixture will normally contain water within the range of about 0.1 to about 2 wt. %.

In accordance with the present invention, the resultant mixture of ethylene glycol with ammonium dimolybdate is heated in the catalyst preparation zone which may suitably comprise an autoclave. The mixture is heated at a temperature between about 50° and about 150° C., and more preferably from 90° to 120° C., preferably at atmospheric pressure for a period of time within the range of about 0.2 to about 2 hours, and more preferably 0.5 to about 1.5 hours in order to react the ammonium dimolybdate with some of the ethylene glycol present in the reaction mixture to form an ethylene glycol solution of an ethylene glycol-ammonium dimolybdate complex. Thereafter, the reaction mixture is cooled and then subjected to a vacuum of 10 to about 100 mm Hg for 30 to 60 minutes while raising the temperature of the reaction medium to about 90° to 110° C. to provide a liquid bottoms product comprising about 80 to about 95 wt. % of the total initial charge weight and having a water content of about 0.1 to about 2 wt. %. This resultant solution of an ethylene glycol/ammonium dimolybdate complex in ethylene glycol will normally contain 6 to about 20 wt. % of molybdenum.

The catalyst preparation zone may suitably be operated as a batch operation and the desired initial ethylene glycol solution may be discharged from the catalyst preparation zone by a line 106 leading to a storage tank 108 from which the ethylene glycol solution may be charged to a reaction zone 10 by a molybdenum catalyst charge line 14.

Suitably, the tertiary butyl hydroperoxide that is charged to the epoxidation reaction zone 10 by way of line 16 is about a 40 to about 75 wt. % solution of tertiary butyl hydroperoxide in tertiary butyl alcohol. The catalyst is charged to the epoxidation reaction zone 10 by the charge line 14 in an amount such as to provide from about 50 to about 1000 ppm of molybdenum, based on the total of the reactants charged and, more preferably, from about 200 to 600 ppm. The epoxidation reaction is preferably conducted at superatmospheric pressure such as a pressure of about 300 to 1000 psig.

Propylene is charged by way of a line 12 to the epoxidation reaction zone 10 in an amount sufficient to provide an initial charge ratio of propylene to tertiary butyl hydroperoxide within the range of about 1.05:1 to about 2:1, and more preferably in the range of about 1.05:1 to about 1.8:1, and still more preferably in the range of about 1.05:1 to about 1.35:1.

When the reaction is conducted on a continuous basis, as illustrated in the drawing, the feed materials are charged to the epoxidation reaction zone 10 through the lines 12, 14 and 16 at rates sufficient to maintain the desired concentration of reactants and an equivalent volume of epoxidation reaction mixture is withdrawn from the epoxidation reaction zone 10 by way of a discharge line 18. The reaction product discharged by the line 18 will normally comprise a minor amount of unreacted propylene, tertiary butyl hydroperoxide, propylene oxide, tertiary butyl alcohol, including tertiary butyl alcohol formed by the reaction of the tertiary butyl hydroperoxide with propylene, the molybdenum catalyst and impurities such as propane, propionaldehyde, acetone, methanol, isopropanol, water, acetaldehyde, methyl formate, acetic acid, formic acid, isobutyric acid, esters, and hydrocarbons containing 6 or more carbon atoms and high boiling residue components.

The reaction product 18 is charged to an epoxidation reaction product distillation zone 20 where it is separated by distillation into desired fractions in accordance with methods known to those skilled in the art. For example, the distillation sequence disclosed in British Pat. No. 1,298,253 may be used.

One of the distillate products that is recovered in the zone 20 is a propylene fraction which is discharged by a line 22 controlled by a valve 24 and provided with a branch line 26 controlled by a valve 28 in order to permit the recycle of unreacted propylene to the epoxidation reaction zone 10 through the propylene charge line 12.

Another distillate fraction that is obtained is a propylene oxide product fraction 30 which is discharged by the line 30.

The propylene oxide fraction may be purified in a propylene oxide purification zone (not shown) by known techniques such as, for example, those disclosed in Burnes et al. U.S. Pat. No. 3,715,284, Schmidt et al. U.S. Pat. Nos. 3,909,366, and 3,881,996, Jubin U.S. Pat. No. 3,607,669, Schmidt U.S. Pat. No. 3,843,488 or 4,140,588.

Another product that is recovered from the epoxidation reaction product distillation zone 20 is a tertiary butyl alcohol distillate product 40 which may be further purified, if desired, to remove oxygenated impurities therefrom by catalytic treatment as disclosed, for example, in Sanderson et al. U.S. Pat. No. 4,704,482, 4,705,903 or 4,742,149.

A heavy distillation fraction 50, usually a bottoms fraction, is also discharged from the epoxidation reaction product distillation zone 20. As described by Levine U.S. Pat. No. 3,819,663 and Sweed U.S. Pat. No. 4,455,283, the heavy distillation fraction will contain substantially all of the molybdenum catalyst initially charged to the epoxidation reaction zone 10 by way of the line 14. The heavy distillation fraction 50 will contain other products such as tertiary butyl hydroperoxide, tertiary butyl alcohol and impurities including oxygenates lighter than tertiary butyl alcohol such as acetaldehyde, acetone, isopropyl alcohol, etc., oxygenates heavier than tertiary butyl alcohol but lighter than tertiary butyl hydroperoxide, and residue components heavier than tertiary butyl hydroperoxide such as propylene glycol tertiary butyl ethers, etc. As indicated, the heavy distillation fraction 50 will also contain carboxylic acids such as formic acid, acetic acid and isobutyric acid and esters.

Although the molybdenum catalyst is present in the epoxidation reaction zone 10 in an amount in the range of about 50 to 1,000 ppm, and usually 200 to 600 ppm, it is progressively concentrated in the epoxidation reaction product distillation zone 20 and is normally present in the heavy distillation fraction 50 in an amount in the range of about 0.4 to 0.8 wt. % (about 4,000 to 8,000 ppm).

The molybdenum-contaminated heavy distillation fraction 50, in accordance with the present invention, is charged to a precipitation zone 60 which may comprise a reaction vessel such as an autoclave which is equipped with suitably agitation means (e.g., an impeller) and suitably temperature control means such as an external jacket or internal coils through which a heat exchange medium can be circulated. Within the precipitation zone the heavy distillation fraction 50 is brought into contact with ammonia which is charged by an ammonia charge line 52 in at least an equimolar amount, based on the molybdenum content of the heavy distillation fraction 50 and, preferably, in a molar excess. The ammonia is preferably used in the form of anhydrous ammonia in order to minimize the water content of the treated heavy distillation fraction 50. The ammonia is suitably brought into contact with the heavy distillation fraction 50 under ambient temperature and pressure conditions, although higher temperatures and/or pressures may be used, such as temperatures within the range of about 20° to 250° C. and pressures within the range of 0 to about 3,000 psig. The contact time should be sufficient to ensure as complete a reaction of the ammonia with the molybdenum as is reasonably possible and to ensure substantially complete precipitation of the product, such as a contact time of about 0.2 to 2 hours.

The thus-formed slurry of precipitate in the treated heavy distillation fraction 50 is discharged from the precipitation zone 60 by a slurry discharge line 62 leading to a precipitate separating zone, such as a filtration zone 70 where the slurry is resolved into a precipitate that is removed by a discharge line 72 and a substantially molybdenum-free filtrate fraction that is discharged by a filtrate discharge line 74 controlled by a valve 76.

The precipitate 72 is then charged to catalyst preparation zone 100 together with ethylene glycol, preferably anhydrous, charged by a line 102. The resultant final catalyst solution is discharged from the catalyst regeneration zone 80 by a line 106 leading to the junction 112 where it is mixed with the initial ethylene glycol solution to provide the catalyst reaction mixture discharge from the junction 112 by the line 14 leading to the epoxidation reaction zone 10.

WORKING EXAMPLES

The following working examples are given by way of illustration and not as limitations in the scope of the invention as claimed herein.

Preparation of Final Catalyst Solution

A series of catalyst compositions (final ethylene glycol solution) were prepared by reacting ethylene glycol with the molybdenum precipitate produced by ammonia treatment of the heavy distillation fraction from epoxidation.

EXAMPLE 1 (No. 6695-1)

About 4.8 g of an ammonium molybdate-containing precipitate containing about 48.4% molybdenum were charged to a 250 ml flask together with 15.0 g of substantially anhydrous ethylene glycol. The flask was equipped with a magnetic stirrer, a K-head, a condenser and a nitrogen purge. The flask was heated to 100° C. and held at this temperature for about 1 hour. Thereafter the contents of the flask were cooled and then subjected to a vacuum to take overhead about 1.3 g of material, leaving a total of 16.5 g of material in the bottom of the flask.

Since the total charge to the flask was 19.8 g, the bottoms resulting after vacuum evacuation amounted to about 83% of the charge. On analysis it was found that a total of 2.323 g of molybdenum were charged and that the molybdenum in the bottoms resulting from vacuum distillation amounted to 2.31 g indicating that 99.4 wt. % of the charged molybdenum was incorporated into the catalyst. The final bottoms was found by analysis to contain 3.17 wt. % of water and the analysis was 14.0 wt. % molybdenum, acid number 160.78, nitrogen (micro Kjeldahl) 0.84.

EXAMPLE 2 (No. 6695-2)

About 6.2 g of an ammonia precipitate containing about 48.0% molybdenum were charged to a 250 ml flask together with 19.2 g of substantially anhydrous ethylene glycol. The flask was equipped with a magnetic stirrer, a K-head, a condenser and a nitrogen purge. The flask was heated to 100° C. and held at this temperature for about 1 hour. Thereafter the contents of the flask were cooled and then subjected to a vacuum to take overhead about 1.7 g of material, leaving a total of 21.2 g of material in the bottom of the flask.

Since the total charge to the flask was 25.4 g, the bottoms resulting after vacuum evacuation amounted to about 83.1% of the charge. On analysis it was found that a total of 2.976 g of molybdenum were charged and that the molybdenum in the bottoms resulting from vacuum distillation amounted to 3.307, indicating an analytical error, because this would indicate that 111% of the charged molybdenum was incorporated into the catalyst. The final bottoms was found by analysis to contain 1.84 wt. % of water and the analysis was 15.6 wt. % molybdenum, acid number 169.36, nitrogen (micro Kjeldahl) 0.72. The analytical error is likely in the Atomic Absorption determination of molybdenum in the catalyst bottoms. The maximum amount of molybdenum that could be in the bottoms (basis the 2.976 g charged) would be 14.0% molybdenum.

EXAMPLE 3 (No. 6695-3)

About 5.0 g of an ammonia precipitate containing about 46.0% molybdenum were charged to a 250 ml flask together with 14.72 g of substantially anhydrous ethylene glycol. The flask was equipped with a magnetic stirrer, a K-head, a condenser and a nitrogen purge. The flask was heated to 100° C. and held at this temperature for about 1 hour. Thereafter the contents of the flask were cooled and then subjected to a vacuum to take overhead about 2.4 g of material, leaving a total of 15.1 g of material in the bottom of the flask.

Since the total charge to the flask was 19.72 g, the bottoms resulting after vacuum evacuation amounted to about 76.6 wt. % of the charge. On analysis it was found that a total of 2.300 g of molybdenum were charged and that the molybdenum in the bottoms resulting from vacuum distillation amounted to 2.356, indicating a small analytical error, because this would indicate that 102.4 wt. % of the charged molybdenum was incorporated into the catalyst. The final bottoms was found by analysis to contain 1.53 wt. % of water and the analysis was 15.6 wt. % molybdenum, acid number 180.54. The maximum amount of molybdenum that could be in the bottoms (basis 2.300 g molybdenum charged) would be 15.23%.

EXAMPLE 4 (No. 6695-4)

About 4.4 g of an ammonia precipitate containing about 5.0% molybdenum were charged to a 250 ml flask together with 14.0 g of substantially anhydrous ethylene glycol. The flask was equipped with a magnetic stirrer, a K-head, a condenser and a nitrogen purge. The flask was heated to 100° C. and held at this temperature for about 1 hour. Thereafter the contents of the flask were cooled and then subjected to a vacuum to take overhead about 1.7 g of material, leaving a total of 14.8 g of material in the bottom of the flask.

Since the total charge to the flask was 18.8 g, the bottoms resulting after vacuum evacuation amounted to about 78.7 wt. % of the charge. On analysis it was found that a total of 2.200 g of molybdenum were charged and that the molybdenum in the bottoms resulting from vacuum distillation amounted to 2.2644 g, indicating a small analytical error, because this would indicate that about 103% of the charged molybdenum was incorporated into the catalyst. The final bottoms was found by analysis to contain 0.04 wt. % of water and the analysis was 15.3 wt. % molybdenum, acid number 162.14, nitrogen (micro Kjeldahl) 0.655. The percent molybdenum in the bottoms (basis 2.20 g molybdenum charged) could be a maximum of 14.86%.

EXAMPLE 5 (No. 6695-5)

About 6.0 g of an ammonia precipitate containing about 47.0% molybdenum were charged to a 250 ml flask together with 18.33 g of substantially anhydrous ethylene glycol. The flask was equipped with a magnetic stirrer, a K-head, a condenser and a nitrogen purge. The flask was heated to 100° C. and held at this temperature for about 1 hour. Thereafter the contents of the flask were cooled and then subjected to a vacuum to take overhead about 2.9 of material, leaving a total of 18.9 g of material in the bottom of the flask.

Since the total charge to the flask was 24.33 g, the bottoms resulting after vacuum evacuation amounted to about 77.7% of the charge. On analysis it was found that a total of 2.820 g of molybdenum were charged and that the molybdenum in the bottoms resulting from vacuum distillation amounted to 2.927, indicating a small analytical error, because this would indicate that 105% of the charged molybdenum was incorporated into the catalyst. The final bottoms was found by analysis to contain 0.11 wt. % of water and the analysis was 15.7 wt. % molybdenum, acid number 173.13, nitrogen (micro Kjeldahl) 1.02. The maximum percent molybdenum that could be in the bottoms would be 14.92% (basis the 2.82 g molybdenum charged).

The results of the foregoing catalyst preparation experiments are summarized in Table I.

TABLE I

Molybdenum Catalyst Preparation from Molybdenum Solids Produced by Ammonia Treatment of Epoxidation Catalyst Bottoms

| NB Run # | ROH | Grams of EG | Moles of EG | Grams Solid (% MO) | Grams Moly (Gr A Moly) | Mole Ratio EG/MO | Rxn Temp °C. | Rxn Time Hrs | Stripping Temp °C. | Time min. (Pressure) |
|---|---|---|---|---|---|---|---|---|---|---|
| 6695-1-2 | EG | 15.00 | 0.242 | 4.80 (48.4) | 2.323 (.024) | 10.00 | 100 | 1.0 | 50-95 | 20 (8-9 mm Hg) |
| 6695-2-2 | EG | 19.20 | 0.309 | 6.20 (48.0) | 2.976 (.031) | 9.97 | 100 | 1.0 | 50-95 | 45 (9 mm Hg) |
| 6695-3-2 | EG | 14.70 | 0.237 | 5.00 (46.0) | 2.300 (.024) | 9.88 | 100 | 1.0 | 35-98 | 20 (9 mm Hg) |
| 6695-4-2 | EG | 14.00 | 0.226 | 4.40 (50.0) | 2.200 (.023) | 9.87 | 100 | 1.0 | 38-94 | 30 (8 mm Hg) |
| 6695-5-2 | EG | 18.30 | 0.295 | 6.00 (47.0) | 2.820 (.029) | 10.03 | 100 | 1.0 | 55-95 | 25 (8 mm Hg) |

| NB Run # | % Moly in Cat | % N2 | % H2O | Acid # | % MOIN | Comments & Observations (Theoretical % Moly) |
|---|---|---|---|---|---|---|
| 6695-1-2 | 14.0 | 0.84 | 3.17 | 160.78 | 99.4 | Starting solids from RAM were 6655-38-12 from liq NH3 treatment of epoxidn cat btms (0.56 wt % moly) Catalyst was clear, brown |
| 6695-2-2 | 15.6 | 0.72 | 1.84 | 169.36 | 110.6 | Starting solids from RAM were 6547-61-8 from liq NH3 treatment of epoxidn cat btms (0.56 wt % moly) Catalyst was clear, brown |
| 6695-3-2 | 15.6 | — | 1.53 | 180.54 | 102.4 | Starting solids from RAM were 6547-63-6 from gaseous NH3 treatment of epoxidn cat btms (0.56 wt % moly) Catalyst was clear, brown |
| 6695-4-2 | 15.3 | 0.66 | 0.04 | 162.14 | 102.9 | Starting solids from RAM were 6547-64-7 from gaseous NH3 treatment of epoxidn cat btms (0.56 wt % moly) Catalyst was clear, brown |
| 6695-5-2 | 15.7 | 1.02 | 0.11 | 173.13 | 105.2 | Starting solids from RAM were 6547-69-5 from liq NH3 treatment of epoxidn cat btms (0.56 wt % moly) Catalyst was clear, brown |

EPOXIDATION EXAMPLES

In the following examples, the catalyst complexes of Examples 1-5 were used to catalyze the reaction of octene-1 with tertiary butyl hydroperoxide. Octene-1 was used rather than propylene for convenience in the laboratory and in order to more conveniently obtain an evaluation of the effectiveness of the catalyst of Examples 1-5. The epoxidation reaction can be run at atmospheric pressure in laboratory glassware when the olefin is octene-1.

The epoxidation results are summarized in attached Table II.

TABLE II

Epoxidation of Octene-1 with Moly/EG Catalysts Made from Moly Solids from Ammonia Treatment of Epoxidation Cat Bottoms

| NB Run # | Oct/TBHP Mole Ratio | Rxn Temp °C. | Rxn Time Hrs. | Catalyst ppm | wt % TBHP in the TBHP/TBA Solution | Octene Area % (GLC) | Octene Oxide Area % (GLC) | wt % TBHP Remaining by Titration | Selectivity to Octene Oxide Basis TBHP Conv | TBHP Conv | Yield Octene Oxide | Conversion of Octene |
|---|---|---|---|---|---|---|---|---|---|---|---|---|
| 6695-7 A | 2.50/1 | 95.0 | 1.0 | .03500 | 73.25 H | 52.486 | 20.085 | 3.02 | 73.32 | 86.44 | 63.36 | 24.18 |

TABLE II-continued

Epoxidation of Octene-1 with Moly/EG Catalysts Made from
Moly Solids from Ammonia Treatment of Epoxidation Cat Bottoms

| NB Run # | Oct/TBHP Mole Ratio | Rxn Temp °C. | Rxn Time Hrs. | Catalyst ppm | wt % TBHP in the TBHP/TBA Solution | Octene Area % (GLC) | Octene Oxide Area % (GLC) | wt % TBHP Remaining by Titration | Selectivity to Octene Oxide Basis TBHP Conv | TBHP Conv | Yield Octene Oxide | Conversion of Octene |
|---|---|---|---|---|---|---|---|---|---|---|---|---|
| 6695-8 B  | " | " | " | " | " | 53.413 | 19.484 | 3.11 | 71.41 | 86.06 | 61.45 | 22.94 |
| 6695-9 C  | " | " | " | " | " | 52.715 | 21.796 | 2.64 | 77.76 | 88.19 | 68.58 | 24.12 |
| 6695-10 D | " | " | " | " | " | 51.749 | 22.271 | 2.47 | 78.88 | 88.94 | 70.16 | 25.43 |
| 6695-11 E | " | " | " | " | " | 53.000 | 20.226 | 3.55 | 75.65 | 84.12 | 63.64 | 23.72 |
| 6695-12 F | " | " | " | " | " | 51.908 | 21.263 | 2.92 | 77.07 | 86.91 | 66.98 | 25.20 |
| 6695-13 F | " | " | " | " | " | 52.733 | 21.289 | 3.32 | 78.66 | 85.15 | 66.98 | 24.10 |
| 6695-14 F | " | " | " | " | " | 52.022 | 21.708 | 2.92 | 78.66 | 86.92 | 68.38 | 25.04 |
| 6695-15 C | " | " | " | .05250 | " | 51.361 | 22.789 | 2.52 | 81.35 | 88.70 | 72.16 | 25.91 |
| 6695-16 D | " | " | " | " | " | 50.378 | 24.273 | 1.98 | 83.38 | 91.19 | 75.99 | 27.85 |
| 6695-19 F | " | " | " | " | " | 51.836 | 22.509 | 3.16 | 82.71 | 85.83 | 70.99 | 25.20 |
| 6695-34 A | " | " | " | .03500 | 58.03 I | 47.577 | 21.481 | 1.12 | 77.06 | 94.60 | 72.90 | 26.25 |
| 6695-35 B | " | " | " | " | " | 46.691 | 22.523 | 1.57 | 82.85 | 92.40 | 76.55 | 27.45 |
| 6695-36 C | " | " | " | " | " | 46.820 | 20.278 | 1.55 | 74.46 | 92.50 | 68.85 | 27.31 |
| 6695-37 D | " | " | " | " | " | 56.675 | 21.895 | 1.46 | 80.20 | 92.95 | 74.55 | 27.36 |
| 6695-38 E | " | " | " | " | " | 47.504 | 21.110 | 1.60 | 77.81 | 92.25 | 71.80 | 26.17 |
| 6695-39 F | " | " | " | " | " | 47.189 | 22.429 | 1.47 | 81.99 | 92.90 | 76.15 | 26.76 |
| 6695-40 F | " | " | " | " | " | 47.318 | 21.923 | 2.29 | 83.88 | 88.93 | 74.60 | 26.42 |
| 6695-41 F | " | " | " | " | " | 47.215 | 21.959 | 1.97 | 82.62 | 90.45 | 74.75 | 26.56 |
| 6695-42 G | " | " | " | " | " | 47.497 | 21.151 | 2.16 | 80.28 | 89.55 | 71.90 | 26.20 |
| 6695-43 G | " | " | " | " | " | 46.857 | 22.799 | 1.94 | 85.46 | 90.65 | 77.45 | 27.22 |
| 6695-44 G | " | " | " | " | " | 47.508 | 21.459 | 2.02 | 80.86 | 90.25 | 73.00 | 26.15 |

A = Catalyst was a moly/EG catalyst made from recovered moly solids (catalyst #6695-1-2).
B = Catalyst was a moly/EG catalyst made from recovered moly solids (catalyst #6695-2-2).
C = Catalyst was a moly/EG catalyst made from recovered moly solids (catalyst #6695-3-2).
D = Catalyst was a moly/EG catalyst made from recovered moly solids (catalyst #6695-4-2).
E = Catalyst was a moly/EG catalyst made from recovered moly solids (catalyst #6695-5-2).
F = Catalyst was a standard moly/EG catalyst (6032-81-2) containing 12.5 wt. % moly.
G = Catalyst was a standard moly/EG catalyst (6488-33-17) made by the pilot plant and used in their unit.
H = TBHP had a water content of 0.41 wt. %.
I = TBHP had a water content of 0.09 wt. %.
In the top section results are within experimental error in terms of selectivity, conversion and yield.
In the bottom section, average selectivities for the 5 recovered catalysts are within experimental error.

A statistical analysis was made of the results reported in Table II. From the statistical analysis it was concluded that:

A) The difference in means for selectivity to octene oxide is statistically significant at the 95-98% probability level for virgin and recycled catalyst. The selectivity is higher with virgin catalyst.

B) The difference in means is not statistically significant for TBHP conversion, octene oxide yield and octene conversion at the 95-98% probability level.

Having thus described our invention, what is claimed is:

1. In a method for the preparation of tertiary butyl alcohol and a $C_3$-$C_{12}$ linear alpha olefin mono epoxide wherein a $C_3$-$C_{12}$ linear alpha mono olefin and tertiary butyl hydroperoxide are reacted in an epoxidation reaction zone in solution in tertiary butyl alcohol in the presence of a catalytic amount of a soluble complex of molybdenum with ethylene glycol to provide an epoxidation reaction product comprising unreacted alpha olefin, unreacted tertiary butyl hydroperoxide, olefin epoxide, tertiary butyl alcohol, dissolved molybdenum-ethylene glycol catalyst complex, and oxygen-containing impurities, and wherein the said epoxidation reaction product is resolved into distillation fractions in a distillation zone, including a distillate alpha olefin fraction, a distillate alpha olefin mono epoxide fraction, a distillate tertiary butyl alcohol fraction and a heavy liquid distillation fraction composed primarily of tertiary butyl hydroperoxide, tertiary butyl alcohol, oxygen-containing impurities and dissolved molybdenum-ethylene glycol catalyst complex, the improvement which comprises the steps of:

a. charging said heavy distillation fraction to a precipitation zone and saturating said heavy distillation fraction in said precipitation zone with ammonia to thereby form a liquid amination product containing a precipitate of solid ammonium-containing molybdenum compounds, b. charging said amination produce to a separation zone and therein separating the solid ammonium-containing molybdenum precipitate therefrom, c. recovering said solid ammonium-containing molybdenum precipitate, d. charging said recovered solid ammonium-containing molybdenum precipitate to a catalyst regeneration zone and mixing it therein with an amount of substantially anhydrous ethylene glycol sufficient to provide about 7 to about 20 moles of ethylene glycol per gram atom of molybdenum contained in said solid ammonium-containing molybdenum precipitate to form an ethylene glycol feed mixture, e. heating said ethylene glycol feed mixture in said catalyst regeneration zone at a pressure of about 0 to 3,000 psig and a reaction temperature of about 70° to about 250° C. for a time within the range of about 1 to 2 hours sufficient to form a substantially solids-free ethylene glycol solution of a complex of ethylene glycol with the ammonium-containing compounds in said solid ammonium-containing molybdenum precipitate, f. holding said solids-free solution of said complex of ethylene glycol with the said ammonium-containing compounds in said catalyst regeneration zone at a temperature of about 90° to about 110° C. for a time, within the range of about 0.5 to 5 hours, sufficient to permit vaporization and removal of volatile by-products, including water, by an amount sufficient to provide an ethylene glycol solution containing about 17 to about 52 wt. % of said complex of ethylene glycol with said ammonium-containing molybdenum compounds and having a molybdenum content of about 6 to about 20 wt. % and a water concentration of about 0.5 to 6 wt. %, and g. charging said thus-prepared ethylene glycol solution of said complex of ethylene glycol with said ammonium-containing molybdenum compounds to said epoxidation reaction zone to catalyze the reaction of additional alpha olefin with additional tertiary butyl hydroperoxide in solution in tertiary butyl alcohol to provide an additional epoxidation reaction product.

2. A method as in claim 1 wherein the alpha olefin is propylene and wherein the heavy liquid distillation fraction is saturated with ammonia in the said precipitation zone under precipitation conditions including a temperature of about 20° to about 250° C. and a pressure of about 0 to about 3,000 psig.

3. A method as in claim 2 wherein the heavy liquid distillation fraction contains from about 0.4 to about 0.8 wt. % of molybdenum, the said filtrate contains about 50 to about 200 ppm of molybdenum and the said precipitated ammonium-containing molybdenum compounds contain about 40 to about 50 wt. % of molybdenum.

4. A method for the molybdenum-catalyzed preparation of tertiary butyl alcohol and propylene oxide from propylene and tertiary butyl hydroperoxide which comprises the steps of:

a. charging substantially anhydrous ethylene glycol and anhydrous ammonium dimolybdate to a catalyst preparation reactor and mixing them therein in amounts sufficient to provide about 7 to about 20 moles of ethylene glycol per gram atom of molybdenum contained in said ammonium dimolybdate, b. heating said mixture of ethylene glycol and said ammonium dimolybdate in said catalyst preparation reactor at a pressure of about 0 to 3,000 psig and a reaction temperature of about 70° to about 250° C. for an amount of time, within the range of about 1 to 2 hours sufficient to form a solids-free solution of a complex of ethylene glycol with said ammonium dimolybdate, c. holding said solids-free solution of said complex of ethylene glycol with the said ammonium dimolybdate in said catalyst preparation reactor at a temperature of about 90° to about 110° C. for a time, within the range of about 0.5 to 5 hours, sufficient to permit vaporization and removal of volatile by-products, including water, by an amount sufficient to provide an initial ethylene glycol solution containing about 80 to about 95 wt. % of said complex of ethylene glycol with said ammonium dimolybdate and having a molybdenum content of about 6 to about 20 wt. % and a water concentration of about 0.5 to 6 wt. %, d. charging a tertiary butyl alcohol solution propylene and tertiary butyl hydroperoxide to an epoxidation reaction zone together with a catalytic amount of a catalyst mixture of (aa) said initial ethylene glycol solution of said complex of ethylene glycol with said ammonium dimolybdate with (bb) a final ethylene glycol solution of a complex of ethylene glycol with ammonium-containing molybdenum compounds derived from a precipitate of solid ammonium containing molybdenum compounds, in amounts sufficient to provide an initial molar ratio of propylene to tertiary butyl hydroperoxide of about 1.05:1 to about 2:1 and a concentration of about 100 to 600 ppm of said catalyst mixture in said tertiary butyl alcohol solution, e. establishing epoxidation reaction conditions in said epoxidation reaction zone including a temperature of about 50° to about 180° C. and a residence time of about 1 to about 5 hours to thereby react said propylene with said tertiary butyl hydroperoxide and form an epoxidation reaction product comprising unreacted propylene, unreacted tertiary butyl hydroperoxide, propylene oxide, tertiary butyl alcohol, dissolved molybdenum-ethylene glycol catalyst complex, and oxygen-containing impurities, f. resolving the said epoxidation reaction product in a distillation zone into distillation fractions including a distillate propylene fraction, a distillate propylene oxide fraction, a distillate tertiary butyl alcohol fraction and a heavy liquid distillation fraction composed primarily of tertiary butyl hydroperoxide, tertiary butyl alcohol, oxygen-containing impurities and dissolved molybdenum-ethylene glycol catalyst complex, g. charging said heavy distillation fraction to a precipitation zone and saturating said heavy distillation fraction in said precipitation zone with ammonia to thereby form a liquid amination product containing a precipitate of solid ammonium-containing molybdenum compounds, h. charging said amination product to a separation zone and therein separating the solid ammonium-containing molybdenum precipitate therefrom, i. recovering said solid ammonium-containing molybdenum precipitate, j. charging said recovered solid ammonium-containing molybdenum precipitate to a catalyst regeneration zone and mixing it therein with an amount of substantially anhydrous ethylene glycol sufficient to provide about 7 to about 20 moles of ethylene glycol per gram atom of molybdenum contained in said solid ammonium-containing molybdenum precipitate to form an ethylene glycol feed mixture, k. heating said ethylene glycol feed mixture in said catalyst regeneration zone at a pressure of about 0 to 3,000 psig and a reaction temperature of about 70° to about 250° C. for a time, within the range of about 0.2 to 2 hours sufficient to form a substantially solids-free ethylene glycol solution of a complex of ethylene glycol with the ammonium-containing compounds in said solid ammonium-containing molybdenum precipitate, l. holding said solids-free solution of said complex of ethylene glycol with the said ammonium-containing compounds in said catalyst regeneration zone at a temperature of about 90° to about 110° C. for a time, within the range of about 0.5 to 5 hours, sufficient to permit vaporization and removal of volatile by-products, including water, by an amount sufficient to provide a final ethylene glycol solution containing about 16 to about 52 wt. % of said complex of ethylene glycol with said ammonium-containing molybdenum compounds and having a molybdenum content of about 6 to about 20 wt. % and a water concentration of about 0.5 to 6 wt. %, and m. charging said thus-prepared final ethylene glycol solution of a complex of ethylene glycol with ammonium-containing molybdenum compounds to said epoxidation reaction zone as said final ethylene glycol solution of a complex of ethylene glycol with ammonium-containing molybdenum compounds derived from a precipitate of solid ammonium containing molybdenum compounds.

5. A method as in claim 4 wherein the heavy liquid distillation fraction is saturated with ammonia in the said precipitation zone under precipitation conditions including a temperature of about 20° to about 250° C. and a pressure of about 0 to about 3,000 psig.

6. A method as in claim 5 wherein the heavy liquid distillation fraction contains from about 0.4 to about 0.8 wt. % of molybdenum, the said filtrate contains about 50 to about 200 ppm of molybdenum and the said precipitated ammonium-containing molybdenum compounds contain about 40 to about 50 wt. % of molybdenum.

7. A continuous method for the molybdenum-catalyzed preparation of tertiary butyl alcohol and propylene oxide from propylene and tertiary butyl hydroperoxide which comprises the steps of:

a. continuously charging substantially anhydrous ethylene glycol and substantially anhydrous ammonium dimolybdate to a catalyst preparation reactor and mixing them therein in amounts sufficient to provide about 7 to about 20 moles of ethylene glycol per gram atom of molybdenum contained in said ammonium dimolybdate, b. continuously heating said mixture of ethylene glycol and ammonium dimolybdate in said catalyst preparation reactor at a pressure of about 0 to 3,000 psig and a reaction temperature of about 70° to about 250° C. for an amount of time, within the range of about 1 to 2 hours sufficient to form a solids-free solution of a complex of ethylene glycol with the said ammonium dimolybdate, c. continuously holding said solids-free solution of said complex of ethylene glycol with ammonium dimolybdate in said catalyst preparation reactor at a temperature of about 90° to about 110° C. for an amount of time, within the range of about 0.5 to 5 hours, sufficient to permit vaporization and removal of volatile by-products, including water, by an amount sufficient to provide an initial ethylene glycol solution containing about 16 to about 52 wt. % of said complex of ethylene glycol with said ammonium dimolybdate and having a molybdenum content of about 6 to about 20 wt. % and a water concentration of about 0.5 to 6 wt. %, d. continuously charging a tertiary butyl alcohol solution of propylene and tertiary butyl hydroperoxide to an epoxidation reaction zone together with a catalytic amount of a catalyst mixture of (aa) said initial ethylene glycol solution of said complex of ethylene glycol with said ammonium dimolybdate with (bb) a final ethylene glycol solution of a complex of ethylene glycol with ammonium-containing molybdenum compounds derived from a precipitate of solid ammonium containing molybdenum compounds, in amounts sufficient to provide an initial molar ratio of propylene to tertiary butyl hydroperoxide of about 1.05:1 to about 2:1 and a concentration of about 100 to 600 ppm of said catalyst mixture in said tertiary butyl alcohol solution, e. establishing epoxidation reaction conditions in said epoxidation reaction zone including a temperature of about 50° to about 180° C. and a reaction time of about 1 to about 5 hours to thereby react said propylene with said tertiary butyl hydroperoxide and form an epoxidation reaction product comprising unreacted propylene, unreacted tertiary butyl hydroperoxide, propylene oxide, tertiary butyl alcohol, dissolved molybdenum-ethylene glycol catalyst complex, and oxygen-containing impurities, f. continuously resolving the said epoxidation reaction product in a distillation zone into distillation fractions including a distillate propylene fraction, a distillate propylene oxide fraction, a distillate tertiary butyl alcohol fraction and a heavy liquid distillation fraction composed primarily of tertiary butyl hydroperoxide, tertiary butyl alcohol, oxygen-containing impurities and dissolved molybdenum-ethylene glycol catalyst complex, g. continuously charging said heavy distillation fraction to a precipitation zone and saturating said heavy distillation fraction in said precipitation zone with ammonia to thereby form a liquid amination product containing a precipitate of solid ammonium-containing molybdenum compounds, h. continuously charging said amination product to a separation zone and therein separating the solid ammonium-containing molybdenum precipitate therefrom, i. continuously recovering said solid ammonium-containing molybdenum precipitate, j. continuously charging said recovered solid ammonium-containing molybdenum precipitate to a catalyst regeneration zone and mixing it therein with an amount of substantially anhydrous ethylene glycol sufficient to provide about 7 to about 20 moles of ethylene glycol per gram atom of molybdenum contained in said solid ammonium-containing molybdenum precipitate to form an ethylene glycol feed mixture, k. continuously heating said ethylene glycol feed mixture in said catalyst regeneration zone at a pressure of about 0 to 3,000 psig. and a reaction temperature of about 70° to about 250° C. for an amount of time, within the range of about 1 to 2 hours sufficient to form a solids-free solution of a complex of ethylene glycol with the ammonium-containing compounds in said solid ammonium-containing molybdenum precipitate, l. holding said solids-free solution of said complex of ethylene glycol with the said ammonium-containing compounds in said catalyst regeneration zone at a temperature of about 90° to about 110° C. for an amount of time, within the range of about 0.5 to 5 hours, sufficient to permit vaporization and removal of volatile by-products, including water, by an amount sufficient to provide a final ethylene glycol solution containing about 16 to about 52 wt. % of said complex ethylene glycol with said ammonium-containing molybdenum compounds and having a molybdenum content of about 6 to about 20 wt. % and a water concentration of about 0.5 to 6 wt. %, and m. continuously charging said thus-prepared final ethylene glycol solution of a complex of ethylene glycol with ammonium-containing molybdenum compounds to said epoxidation reaction zone as said final ethylene glycol solution of a complex of ethylene glycol with ammonium-containing molybdenum compounds derived from a precipitate of solid ammonium containing molybdenum compounds.

8. A method as in claim 7 wherein the heavy liquid distillation fraction is saturated with ammonia in the said precipitation zone under precipitation conditions including a temperature of about 20° to about 250° C. and a pressure of about 0 to about 3,000 psig.

9. A method as in claim 8 wherein the heavy liquid distillation fraction contains from about 0.4 to about 0.8 wt. % of molybdenum, the said filtrate contains about 50 to about 200 ppm of molybdenum and the said precipitated ammonium-containing molybdenum compounds contain about 40 to about 50 wt. % of molybdenum.

* * * * *